United States Patent [19]

Young

[11] Patent Number: 4,784,868

[45] Date of Patent: Nov. 15, 1988

[54] POTABLE SPIRIT PRODUCTION

[75] Inventor: Albert T. Young, Tullibody, Scotland

[73] Assignee: United Distillers P.L.C., Scotland

[21] Appl. No.: 4,949

[22] Filed: Jan. 20, 1987

[30] Foreign Application Priority Data

Jan. 17, 1986 [GB] United Kingdom ................. 8601082

[51] Int. Cl.[4] .......................... C12G 3/00; B01D 3/14
[52] U.S. Cl. .................................... 426/493; 426/592;
                203/19; 203/43; 203/71; 203/DIG. 13;
                210/634; 210/640; 568/916
[58] Field of Search .................... 203/19, 45, DIG. 13,
            203/18, 43, 99, DIG. 19, 71; 426/493, 592;
            435/161; 568/913, 916; 210/640, 634; 55/75

[56] References Cited

U.S. PATENT DOCUMENTS

| | | | |
|---|---|---|---|
| 2,880,091 | 3/1959 | Neureuther | 426/494 |
| 3,930,042 | 12/1975 | Dunnet | 426/493 |
| 4,217,178 | 8/1980 | Katzen et al. | 203/DIG. 13 |
| 4,256,541 | 3/1981 | Muller et al. | 203/DIG. 13 |
| 4,273,621 | 6/1981 | Fornoff | 203/19 |
| 4,297,172 | 10/1981 | Kyle | 203/19 |
| 4,399,000 | 8/1983 | Tedder | 203/19 |
| 4,405,409 | 9/1983 | Tusel et al. | 203/19 |
| 4,420,561 | 12/1983 | Chen et al. | 435/161 |
| 4,492,808 | 1/1985 | Hagen et al. | 568/916 |
| 4,510,242 | 4/1985 | Tedder | 203/DIG. 13 |
| 4,511,437 | 4/1985 | Heck et al. | 203/19 |
| 4,541,897 | 9/1985 | Sommer et al. | 203/DIG. 13 |
| 4,556,460 | 12/1985 | Robertson et al. | 203/DIG. 13 |

FOREIGN PATENT DOCUMENTS

| | | | |
|---|---|---|---|
| 0031097 | 7/1981 | European Pat. Off. | 203/DIG. 13 |
| 122539 | 10/1984 | European Pat. Off. | |
| 158754 | 10/1985 | European Pat. Off. | |
| 3113223 | 10/1982 | Fed. Rep. of Germany | 203/19 |
| 0055001 | 4/1983 | Japan | 203/19 |
| 0564870 | 7/1977 | U.S.S.R. | 203/19 |
| 0615131 | 7/1978 | U.S.S.R. | 203/DIG. 13 |
| 1148864 | 4/1985 | U.S.S.R. | 203/19 |
| 0399281 | 10/1933 | United Kingdom | 203/19 |

OTHER PUBLICATIONS

Annex I to amended proposal for Counsel Regulation (EEC), Official J. European Communities, No. C 269/4 (10-1986).
"Pervaporation Cracks Age-Old Distillation Problems", *Processing*, (Mar. 1986).

*Primary Examiner*—David L. Lacey
*Assistant Examiner*—V. Manoharan
*Attorney, Agent, or Firm*—Sughrue, Mion, Zinn, Macpeak, and Seas

[57] ABSTRACT

A method of producing a potable spirit comprises removing water from a fermented wash containing ethanol, water and congeners to produce a substantially water-free mixture of ethanol and congeners, and then fractionally distilling this water-free mixture of ethanol and congeners in the absence of water to produce a fraction containing substantially pure water-free potable ethanol. Preferably the fractional distillation is carried out in separate topping and tailing columns. This method provides an energy efficient separation of the ethanol and congeners.

12 Claims, 2 Drawing Sheets

CO₂ EXTRACTION PROCESS

POTABLE SPIRIT PRODUCTION

BACKGROUND OF THE INVENTION

At present potable spirits are invariably produced by an initial fermentation process involving the fermentation of a carbohydrate rich feed stock to produce a wash having an alcohol concentration of between 6% and 12% weight for weight. This wash is then distilled to produce a distilled raw spirit containing an ethanol water mixture which may approach azeotrope strenght, and typically contain 92% weight for weight ethanol. The distilled raw spirit also contains various congeners such as fusel oils and higher alcohols which are carried over during the distillation process despite having higher boiling points.

When manufacturing a white spirit such as vodka or gin the distilled raw spirit may be subjected to further operations such as subjecting it to the hydroselection process in which the distilled raw spirit is diluted with water and then redistilled. This hydroselection process helps to remove the congeners that are unwanted in white spirit but substantially increases the energy requirements for distillation. The final spirit which is obtained is an ethanol and water azeotrope. This may then be passed through adsorbent material such as active carbon to remove the remaining congeners to provide a substantially pure ethanol in the production of vodka or receive further rectification and flavoring treatment in the production of gin. The final spirit is diluted with demineralised water before retail distribution. Alternatively the pure ethanol is used as a spirit base for fortification or in the production of other alcoholic drinks.

In the production of industrial ethanol when it is required to produce substantially water free ethanol this is usually achieved by adding a material such as benzene to the ethanol water azeotrope to provide a ternary system. Subsequent distillation of this ternary system provides substantially water-free ethanol. However, this substantially water-free ethanol is contaminated with benzene. Such contamination would be totally unacceptable in the preparation of a potable spirit.

SUMMARY OF THE INVENTION

According to this invention in the production of a potable spirit, water is removed from a fermented wash containing ethanol, water and congeners to produce a substantially water-free mixture of ethanol and congeners, and then this water-free mixture of ethanol and congeners is fractionally distilled in the absence of water to produce a fraction containing water-free potable ethanol.

By removing the water from the fermented wash to leave solely a mixture of ethanol and the congeners it is possible to carry out an effective fractional distillation. Using this technique it is possible to reduce the energy requirements for distillation, particularly as compared to the conventional hydroselection techniques, and yet provide an ethanol fraction which exceeds the EEC standard of purity for potable spirtous beverages. This standard for ethyl alcohol of agricultural origin is defined in Annex I to the ammended proposal for a Council Regulation (EEC) laying down general rules on the definition, description and presentation of spiritous beverages; published in the Official Journal of the European Communities, No. C 269/4 dated 25.10.1986. The process in accordance with the invention is particularly attractive for the production of a white spirit such as vodka or gin but may also be used for other beverages. A further advantage of this method is that the congeners such as the fusel oils are obtained in a concentrated and dehydrated form and so produce useful by-products.

The fractional distillation of the substantially water-free ethanol and congener mixture may take place in a single multiplate distillation column. This does not provide a perfect separation of the congeners from the ethanol but does produce ethanol which is low in congeners. Such a product is perfectly satisfactory if, for example, it is to be used to fortify wines, or produce a spiritous beverage in which some congeners are either required to impart a particular flavor, or their flavor is masked. However, if the ethanol is to be used in the production of a white spirit it is preferred that the fractional distillation process is carried out in separate topping and tailing columns.

The water-free mixture of ethanol and congeners ay be fed in towards the base of the topping column and, in this case a top product of high feints which is rich in methanol, ethyl acetate, acetaldehyde and diecetal is obtained. The bottoms product of the topping column is then fed into the tailing column towards its base. A top product containing remaining high feints is obtained whilst the substantially pure ethanol is obtained a few plates lower. A bottom product rich in low feints, mainly the higher alcohols such as iso-amyl alcohol, isobutyl alcohol, propanols, butanols and pentanols, fatty acid esters, ethyl lactate, and furfural is obtained as a bottoms product from the tailing column.

Alternatively, the water-free mixture of ethanol and congeners may be fed in to the tailing column. A top product of high feints is obtained but a main product is taken off from a plate towards the top of the tailing column and then fed into the topping column. The bottom product of the tailing column is rich in low feints. In the topping column a top product rich in high feints is obtained and the substantially pure ethanol is obtained as the bottoms product.

The topping and tailing columns each preferably have a minimum of forty plates and a product including less congeners can be obtained if the number of plates is increased to sixty.

Preferably the water is removed from the fermented wash by an extraction process in which ethanol is preferentially taken into solution in liquid carbon dioxide and a molecular sieve dryer is used to remove the water remaining in the solution. In this case, the ethanol content of the ethanol/water mixture is preferably at least 40% w/w and more preferably at least 70% w/w. It is especially preferred that the ethanol content of the mixture is substantially 80% w/w before being contacted with the liquid carbon dioxide. Typically a fermented wash has an ethanol content of between 6% w/w and 12% w/w. Before such a wash can have water removed from it economically by such a method the fermented wash must be subjected to an initial concentration process.

The initial concentration process may have the form of a simple distillation carried out in a wash still which strips substantially all of the ethanol from the fermented wash or it may include some rectification and reflux stages to increase the ethanol content to a higher level and typically to between 70 and 80% w/w of ethanol. It is also possible to provide a continuous fermentation and primary distillation step in which a continuous fermentation process is employed with a substrate to be fermented being introduced continuously into a fermenter and the resulting fermented wash being passed through a vaporizer providing an output of between 30% and 40% ethanol w/w. A part of the stripped wash is then returned to the fermenter and the remainder is concentrated and discharged as stillage.

It is preferred that the carbon dioxide produced during the fermentation of, for example, a cereal product, is used to provide the liquid carbon dioxide used in the extraction process, and it is preferred that dry substantially pure carbon dioxide is produced as an additional product by recovering it as a product after separating it from the ethanol. In this case a carbon dioxide outlet from the fermenter is fed to a carbon dioxide compressor and the outlet of this is fed to a cooler. The cooler may provide the heat required to regenerate the molecular sieve dryer.

A full discussion and description of the method and apparatus for obtaining dry ethanol and congener mixture using liquid carbon dioxide is contained in common assignee co-pending patent application U.S. Ser. No. 07/004,447, which claims priority from British Patent Application No. 8601081.

As an alternative to the method described above for the removal of water from the fermented wash it is also possible to separate the water and ethanol by pervaporation. The pervaporation technique is described in an article entitled "Pervaporation cracks age-old distillation problems" by Jin Lock published in Processing, March 1986 issue. In pervaporation a permeable membrane is exposed to an ethanol water vapor usually of azeotrope strength. The membrane is preferentially permeable by the water and, with appropriate recirculation, condensation and fractionation, it is possible to obtain substantially water-free ethanol and congener mixture.

BRIEF DESCRIPTION OF THE DRAWINGS

Particular examples of methods in accordance with this invention will now be described with reference to the accompanying drawings, in which.

Figure 1:
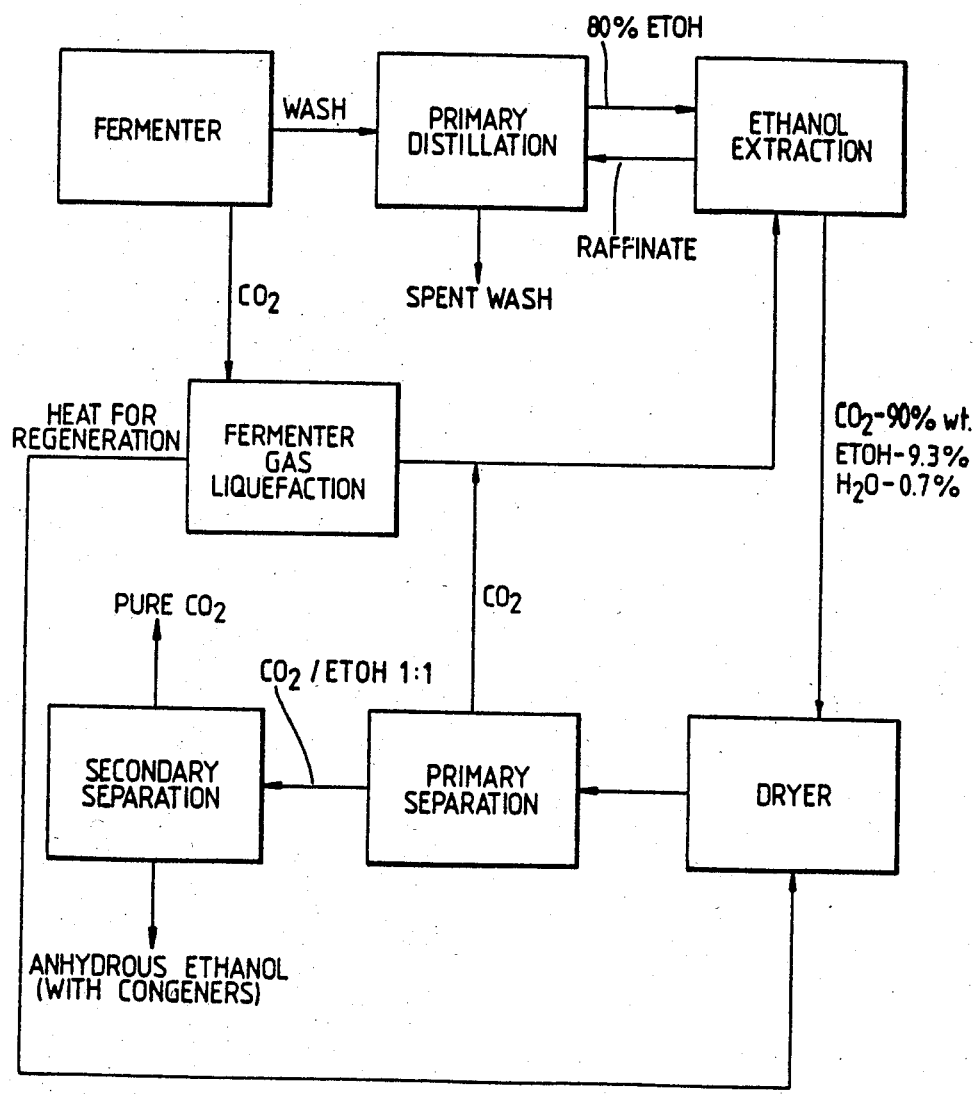
FIG. 1 is a schematic diagram of a carbon dioxide extraction process for obtaining a substantially dry mixture of ethanol and congener.
Figure 2:
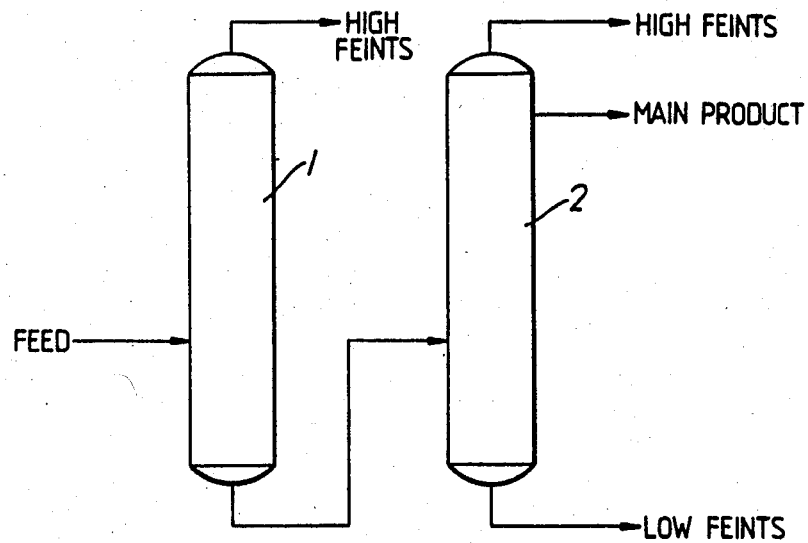
FIG. 2 is a diagram of a first fractional distillation system.
Figure 3:
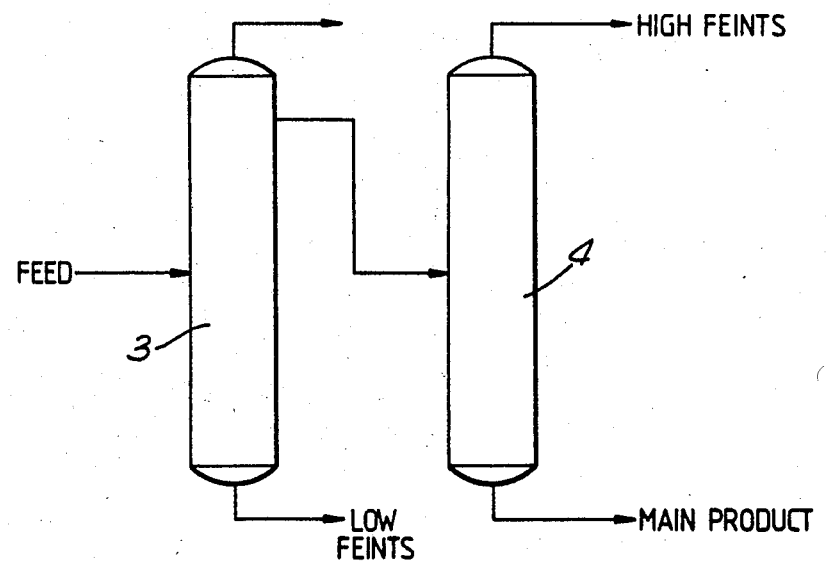
FIG. 3 is a diagram of a second example of fractional distillation system.

ethanol. The carbon dioxide evolved from the fermentation process is compressed and liquefied. The fermented wash is distilled in a simple, primary distillation plant to produce an ethanol water mixture which typically consists of about 80% by weight of ethanol. This mixture is pumped into a contaction column in which it moves in counter-current with the flow of the liquefied carbon dioxide. Ethanol and congeners are preferentially taken into solution with liquid carbon dioxide and a carbon dioxide solution rich in ethanol and typically containing 90% w/w carbon dioxide, 9.3% w/w ethanol plus congeners and 0.7% w/w water, leaves the top of the contaction column.

This solution rich in ethanol is then dehydrated by passage through a molecular sieve formed by a crystalline zeolite having a nominal pore aperture size of 3 Angstroms (0.3 nm). The dry solution is then concentrated by evaporating carbon dioxide vapor in a primary separation system. This vapor is recompressed and reliquefied and recycled to the contaction column. Typically the heat required to evaporate the carbon dioxide vapor is provided by the heat liberated upon condensing the recompressed carbon dioxide vapor to reform liquid carbon dioxide. The product of this primary separation process has an ethanol concentration of at least 30% w/w and preferably 50% by weight ethanol. This solution is separated in a secondary separation system consisting of a simple distillation column to produce a dry carbon dioxide product as a top product and an anyhdrous ethanol and congener mixture as a bottoms product.

To separate the ethanol from the congener in a first example the bottoms product obtained from the secondary separation system is fractionally distilled in a distillation system comprising a topping column 1 followed by a tailing column 2. In this experimental scale process two Odershaw columns two inches (50 mms) in diameter and each containing forty plates were used as the topping 1 and tailing 2 columns. The anhydrous ethanol and congener mixture was fed to plate 15 of the topping column 1. The bottoms product from the column 1 is then fed into plate 15 of the tailing column 2. The final product was taken from plate 35 of the tailing column 2. A top product of high feints is obtained from the top of the topping column 1 and a small amount of high feints is also obtained as a top product from tailing column 2. The bottoms product from tailing column 2 consists of low feints.

Table 1 sets out the concentrations of the congeners at various points in the fractional distillation system.

TABLE 1

|  | Feed To Column 1 | Top Product Column 1 | Bottoms Product 1 and Feed to Column 2 | Top Product Column 2 | Bottom Product Column 2 | Main Product from Column 2 |
|---|---|---|---|---|---|---|
| ethyl acetate | NA | NA | 0.05 | 0.5 | ND | 0.25 |
| isoamyl acetate | 0.04 | ND | 0.06 | ND | 0.48 | ND |
| acetal | NA | NA | 0.3 | 0.7 | 0.9 | 0.5 |
| n-propanol | NA | NA | 8.7 | ND | 95.3 | ND |
| isobutyl alcohol | NA | NA | 1.5 | ND | 54.4 | ND |
| isoamyl alcohols | NA | NA | 3.7 | ND | 75.6 | ND |
| ethyl propionate | 0.1 | 1.05 | 0.11 | 0.22 | 0.04 | 0.05 |
| ethyl n-butyrate | 0.79 | ND | 8.4 | 0.12 | 0.95 | 0.55 |
| isobutyl acetate | 0.08 | 0.04 | 0.11 | 0.03 | 0.14 | 0.085 |

Where NA = not analysed; ND = not detected and all concentrations are given in g/hl.

DESCRIPTION OF PARTICULAR EXAMPLES

A carbohydrate feedstock is fermented by yeast in a fermenter to produce a product containing 6% w/w Table 1 illustrates how the congeners are concentrated in the top product of columns 1 and 2 and in the bottoms product of column 2 and illustrate the low concentration of congener in the main product taken from plate 35 of column 2.

In a second example the output from the secondary separation system of liquid carbon dioxide extraction system was first fed into a tailing column 3 and then a main product from this tailing column fed to a topping column 4. Again two Oldershaw columns of 2 inches (50 mm) diameter each containing forty plates were used as the tailing 3 and topping 4 columns. Typically the feed was introduced at plate 20 of tailing column 3 and the main product removed from plate 35 of tailing column 3. A top product of high feints and a bottoms product of low feints was obtained from the column 3. The main product from plate 35 of column 3 was then fed to plate 20 of column 4. A top product of high feints was removed from column 4 and a bottoms product of column 4 forms the final product. The results of analyses obtained at various points in this fractional distillation system are shown in Table 2.

TABLE 2

|  | Feed to Column 3 | Bottom Product Column 3 | Main Product Column 3 and Feed to Column 4 | Main Product Column 4 | Top Product Column 4 |
|---|---|---|---|---|---|
| ethyl acetate | 2.25 | Tr | 1.8 | 0.03 | 27.4 |
| isoamyl acetate | 0.17 | 0.48 | 0.06 | 0.06 | ND |
| acetal | 0.65 | 0.26 | 0.92 | 0.55 | 9.4 |
| n propanol | 3.2 | 8 | 0.1 | 1.1 | ND |
| iso butanol | 0.6 | 1.9 | ND | ND | ND |
| isoamyl alcohols | 1.5 | 60 | ND | ND | ND |
| methanol | 3.1 | 0.25 | 2.45 | 1.78 | 18.5 |
| acetaldehyde | 0.58 | ND | 0.29 | ND | 4.4 |
| ethyl n propionate | NA | NA | 0.12 | 0.065 | 0.89 |
| ethyl isobutyrate | NA | NA | 0.01 | 0.01 | 0.02 |
| isobutyl acetate | NA | NA | 0.13 | 0.1 | 0.05 |
| ethyl n-butyrate | NA | NA | 0.053 | 0.05 | 0.08 |
| n-propyl propionate | NA | NA | ND | ND | ND |
| iso-amyl acetate | NA | NA | 0.03 | 0.04 | <0.01 |
| ethyl hexanoate | NA | NA | 0.14 | 0.05 | ND | where NA = not analysed; ND = not detected; Tr = trace; and all concentrations are given in g/hl.

This table again shows how the congeners are concentrated in the top product from column 3 and 4 and the bottoms product from column 3 and 4 and illustrate the low concentration of congeners in the final product obtained as a bottoms product from column 4.

I claim:

1. A method of producing a potable spirit comprising providing a fermented wash containing ethanol, water and congeners, removing water from said fermented wash, to produce a substantially water-free mixture of ethanol and congeners, and then fractionally distilling said water-free mixture of ethanol and congeners in the absence of water to produce a potable spirit fraction containing water free potable ethanol.

2. A method according to claim 1, wherein said fractional distillation of said substantially water-free mixture of ethanol and congeners takes place in a single multiplate distillation column.

3. A method according to claim 1, wherein said fractional distillation process is carried out in separate topping and tailing columns to obtain potable ethanol.

4. A method according to claim 3, wherein said substantially water-free mixture of ethanol and congeners is initially fractionally distilled in said topping column and then fed into said tailing column, said potable ethanol being taken from a region towards, but not at a top of, said tailing column.

5. A method according to claim 4, wherein said water is removed from said fermented wash by an extraction process using liquid carbon dioxide and by a molecular sieve drying process.

6. A method according to claim 5, wherein said ethanol content of said fermented wash is at least 70% w/w before being subjected to said carbon dioxide extraction process.

7. A method according to claim 4, in which said water is removed from said fermented wash using a permeable membrane.

8. A method according to claim 3, wherein said substantially water-free mixture of ethanol and congeners is initially fractionally distilled in said tailing column and then fed into said topping column, said potable ethanol being taken from a bottom of said topping column.

9. A method according to claim 8, wherein said water is removed from said fermented wash by an extraction process using liquid carbon dioxide and drying process by a molecular sieve.

10. A method according to claim 9, wherein said ethanol content of said fermented wash is at least 70% w/w before being subjected to said carbon dioxide extraction process.

11. A method according to claim 8, in which said water is removed from said fermented wash using a permeable membrane.

12. A method according to claim 1, in which said water is removed from said fermented waws using a permeable membrane.

* * * * *